United States Patent
Dalloro et al.

(10) Patent No.: US 6,936,738 B2
(45) Date of Patent: Aug. 30, 2005

(54) PROCESS FOR THE PREPARATION OF PHENOL BY MEANS OF THE HYDRODEOXYGENATION OF BENZENE-DIOLS

(75) Inventors: Leonardo Dalloro, Bollate (IT);
Alberto Cesana, Carate Brianza (IT);
Roberto Buzzoni, San Mauro Torinese (IT); Franco Rivetti, Milan (IT)

(73) Assignees: ENI S.p.A., Rome (IT); Polimeri Europa S.p.A., Brindisi (IT)

( * ) Notice: Subject to any disclaimer, the term of this patent is extended or adjusted under 35 U.S.C. 154(b) by 0 days.

(21) Appl. No.: 10/683,403

(22) Filed: Oct. 14, 2003

(65) Prior Publication Data

US 2004/0077906 A1 Apr. 22, 2004

(30) Foreign Application Priority Data

Oct. 15, 2002 (IT) .................................... MI2002A2185

(51) Int. Cl.$^7$ ............................................. C07C 39/00
(52) U.S. Cl. ..................................... 568/716; 568/799
(58) Field of Search ................................. 568/716, 799

(56) References Cited

U.S. PATENT DOCUMENTS 6,133,487 A * 10/2000 Ungarelli et al. ........... 568/803

FOREIGN PATENT DOCUMENTS

DE 849 557 9/1952

* cited by examiner

Primary Examiner—Michael L. Shippen
(74) Attorney, Agent, or Firm—Oblon, Spivak, McClelland, Maier & Neustadt, P.C.

(57) ABSTRACT

A process is described for the preparation of phenol characterized in that the phenol is obtained by means of the hydrodeoxygenation of benzene-diols with hydrogen, operating in continuous, in an aqueous solution, at temperatures ranging from 250 to 500° C., at pressures of 1–100 bar and in the presence of a catalyst based on elements of group VIB or group VIII of the periodic table.

23 Claims, 1 Drawing Sheet

SCHEME OF THE EQUIPMENT FOR THE HYDRODEOXYGENATION OF BENZENE-DIOLS IN TWO STEPS

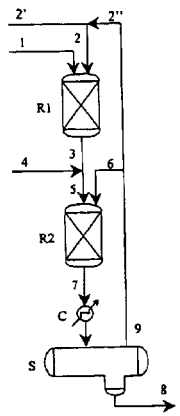

R1  First reactor
R2  Second reactor
C   Condenser
S   Gas-liquid separator
1.  Benzene-diols in aqueous solution, feeding to R1
2.  Hydrogen feeding to R1
2'. Fresh hydrogen, feeding to R1
2". Recycled hydrogen, feeding to R1
3.  Stream leaving R1
4.  Cooling water
5.  Cooled mixture, feeding to R2
6.  Recycled hydrogen, feeding to R2
7.  Stream leaving R2
8.  Aqueous solution of raw phenol
9.  Hydrogen for recycling.

FIGURE 1
SCHEME OF THE EQUIPMENT FOR THE HYDRODEOXYGENATION OF BENZENE-DIOLS IN TWO STEPS

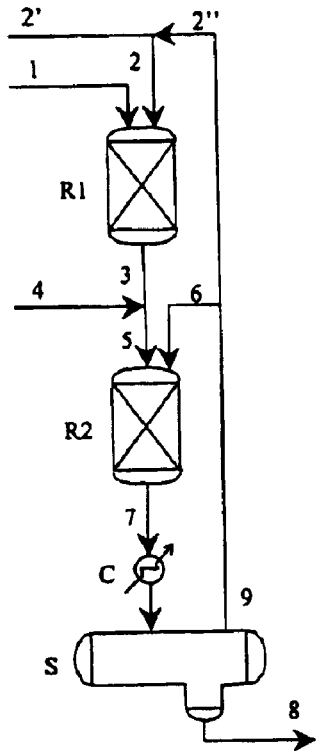

R1   First reactor
R2   Second reactor
C    Condenser
S    Gas-liquid separator
1.   Benzene-diols in aqueous solution, feeding to R1
2.   Hydrogen feeding to R1
2'.  Fresh hydrogen, feeding to R1
2".  Recycled hydrogen, feeding to R1
3.   Stream leaving R1
4.   Cooling water
5.   Cooled mixture, feeding to R2
6.   Recycled hydrogen, feeding to R2
7.   Stream leaving R2
8.   Aqueous solution of raw phenol
9.   Hydrogen for recycling.

PROCESS FOR THE PREPARATION OF PHENOL BY MEANS OF THE HYDRODEOXYGENATION OF BENZENE-DIOLS

The present invention relates to a process for the preparation of phenol by means of the catalytic hydrodeoxygenation of benzene-diols.

More specifically, the present invention relates to a continuous process for the preparation of phenol by means of the hydrodeoxygenation of benzene-diols with hydrogen, carried out in aqueous solution in the presence of a catalyst based on elements of group VIB or group VIII of the periodic table.

Phenol is an extremely important industrial intermediate, used for example in the production of polycarbonates or other phenol resins.

Benzene-diols at a low valorization are available as derivatives of a natural origin or as by-products of industrial chemical processing.

Hydrodeoxygenation reactions are described by E. Furimsky in CATAL. REV. -SCI. ENG., 25(3), 421–458 (1983).

Furimsky describes a synthesis of the works published in the field of hydrodeoxygenation and in particular reactions carried out on raw materials used for the production of liquid fuels or on model compounds.

Hydrodeoxygenation reactions are, in fact, mainly applied to the treatment of raw materials destined for the production of fuels, aimed at a complete and exhaustive deoxygenation of the reagent substrates, as the presence of oxygen in these liquid fuels is undesirable. The oxygen content in these raw materials may be considerable and is generally due to the presence of hydroxyl, carbonyl, carboxyl, ether, ketone groups, etc. Among the most widely studied raw materials, liquids deriving from the liquefaction of carbon in which the oxygen content is mainly caused by the presence of phenol groups, are mentioned (page 434).

Among model compounds used for the study of hydrodeoxygenation reactions, o- and p-cresol, naphthol, phenol, o-phenylphenol and other phenols, are mentioned (Table 5, 442).

Phenols, in relation to their structure, may require, for a complete deoxygenation, in addition to the presence of a reducing agent, also the presence of a catalyst (Table 2, page 429).

Hydrodeoxygenation reactions can be carried out in the presence of numerous catalysts even though those containing Mo or W combined with Ni or Co as promoters, have often proved to be more effective; for compounds of the phenol type, catalysts based on Th and Pt oxide have also proved to be useful (page 444).

One of the drawbacks observed in hydrodeoxygenation reactions is the deactivation of the catalyst due to the presence of water which is formed during the reaction (page 455).

A process has now been found which is based on a partial and selective hydrodeoxygenation reaction effected with hydrogen in the presence of a catalyst based on elements of group VIB or group VIII of the periodic table and which allows benzene-diols to be transformed into phenol with high conversions, selectivities and productivities, operating in aqueous solution.

This is a surprising result, above all in view of the previous observations which identify water as being the agent responsible for the poisoning of the catalyst in hydrodeoxygenation reactions.

In the reaction in question, moreover, in which the substrate to be subjected to deoxygenation consists of benzene-diols, the use of water as solvent has numerous advantages both from a technical and economic point of view. Water can, in fact, keep high concentrations of both reagents and products, in solution. Furthermore, water is completely inert towards reagents and products in the reaction environment. As a reaction solvent, water also has the advantage of having high thermal capacities and consequently the property of limiting a temperature increase due to the enthalpy of the deoxygenation reaction. Finally, water is particularly inexpensive.

In its widest aspect, the invention relates to a process for the preparation of phenol characterized in that phenol is obtained by means of the hydrodeoxygenation of benzene-diols with hydrogen, operating in continuous, in aqueous solution, at temperatures ranging from 250 to 500° C., at pressures of 1–100 bar and in the presence of a catalyst based on elements of group VIB or their mixtures or group VIII of the periodic table or their mixtures.

Operating according to the process of the present invention, it is possible to convert to phenol with a high efficiency and selectivity 1,2-benzene-diol (catechol, indicated hereunder for the sake of brevity 1,2-BD), 1,3-benzene-diol (resorcinol, hereunder 1,3-BD), 1,4-benzenediol (hydroquinone, hereunder 1,4-BD) and their mixtures.

The reaction is carried out in vapour phase at a temperature of 250–500° C., preferably 300–450° C., at a pressure of 1–100 bar, preferably from 3–50 bar, and a space velocity (WHSV=Weight Hourly Space Velocity, expressed as kg of benzene-diols/h/kg of catalyst) of 0.1–10 $h^{-1}$, preferably 0.5–5 $h^{-1}$.

In particular, the feeding of the reactor consists of a solution of benzene-diols in water at a concentration of 5–60% by weight, preferably 10–40% by weight, and hydrogen with a molar ratio with respect to benzene-diols of 2–50, preferably 5–30.

The catalyst can be selected from those for hydrodeoxygenation based on elements of group VIB or group VIII of the periodic table.

When the catalyst is based on elements of group VIB, it can contain, as promoters, elements belonging to group VIII and phosphorous. The elements of group VIB can be used in a mixture and, among these, molybdenum and tungsten are preferred. Among promoters of group VIII, nickel, cobalt, iron and ruthenium are preferred and can be used in a mixture with each other and with phosphorous.

When the catalyst is based on elements of group VIII, it can contain, as promoters, zinc, rhenium, selenium, tin, germanium and lead. The elements of group VIII can be used in a mixture and, among these, cobalt, palladium, nickel and platinum are preferred. The promoters can also be mixed with each other.

The active phase is preferably deposited on a carrier. Preferred carriers are inorganic oxides such as alumina, silica, titanium dioxide, crystalline or amorphous aluminosilicates, crystalline spinels having the general formula $F^{2+}R_2^{3+}O_4$ (wherein $F^{2+}$ can be Mg, Fe, Zn, Mn, Ni, etc., and $R^{3+}$ can be Al, Fe, Cr, etc.) or their mixtures. The typical surface area of these materials ranges from 1 to 800 $m^2/g$, preferably from 10 to 500 $m^2/g$, the pore volume is 0.05–2 $cm^3/g$, preferably between 0.1 and 1.5 $cm^3/g$. The catalysts and carriers can be in a suitable form for use, for example, in a fixed bed reactor: extruded products, tablets, spheres, with a size ranging from 1 to 12 mm are suitable for the purpose.

For catalysts based on an element of group VIB, said element is generally present on the carrier in a concentration ranging from 1 to 50% by weight, preferably from 3–30% by weight. The promoters of these catalysts are generally present at concentrations ranging from 0.1 to 100% atomic with respect to the element of group VIB, preferably from 1 to 50%. Without establishing any limitation to the possible compositions, or indicating any preferences, examples of these catalysts are Mo, W, CoMo, NiMo, NiW, FeMo, RuMo, CoMoP, NiMoP, CoWMo, CoWMoP.

Before being used in the reaction, these catalysts can be subjected to treatment for modifying their chemical characteristics, for example sulphuration with $H_2S$, dimethylsulfide, dimethyldisulfide, carbon sulfide or other compounds useful for the purpose.

For catalysts based on an element of group VIII, said element is generally present on the carrier in a concentration ranging from 0.05 to 20% by weight, preferably from 0.1–10% by weight. The promoters of these catalysts are generally present at concentrations ranging from 0.5 to 200% atomic with respect to the element of group VIII, preferably from 1 to 120%. Without establishing any limitation to the possible compositions, or indicating any preferences, examples of these catalysts are Pt, Pd, Co, Ni, PtZn, PtRe, PtNi, PtSe, PtSn, PtGe, PdPb, PdSn.

The catalysts object of the invention can be prepared with the incipient wetness technique or by absorption from solution.

The former method comprises impregnation of a porous carrier with a volume of solution, containing the soluble precursors of the active phases, equal to the volume of the pores of the carrier used. In this way, the precursors present in solution are quantitatively absorbed by the carrier. In order to reach the desired charge of elements, the procedure can be repeated several times, alternating it with drying.

The second method involves absorption on the carrier of the precursors of the active phase starting from a solution in which the carrier is dispersed.

Among the precursors which can be used, ammonium heptamolybdate tetrahydrate, cobalt nitrate hexahydrate, nickel nitrate hexahydrate, iron nitrate nonahydrate, ruthenium chloride, commercial solutions of hexachloroplatinic acid (Pt 7.7%), can be mentioned, according to what is disclosed in the state of the art, The impregnated carrier can be subjected to chemical treatment, optionally alternating with thermal treatment. A typical chemical treatment consists, for example, in the reduction of the carrier, impregnated with hexachloroplatinic acid, with a solution of sodium formiate at 85–95° C.

A final thermal treatment always completes the preparation.

In an embodiment of the invention, the reaction is carried out inside an adiabatic fixed bed reactor containing a catalyst as described above, in which a stream containing an aqueous solution of benzene-diols is fed, at concentrations ranging from 5 to 60% by weight, together with a stream of hydrogen in such a quantity that the ratio between the total moles of hydrogen and benzene-diols ranges from 2:1 to 50:1. The feeding is vaporized and heated to a temperature ranging from 250 to 500° C. and the pressure is kept between 1 and 100 bar. The stream leaving the reactor consists of the reaction raw product, comprising possible residual benzene-diols and the phenol produced in aqueous solution, and residual hydrogen which is recycled.

In another embodiment of the invention, the reaction is carried out in two or more adiabatic fixed bed reactors in series, in order to cool the stream leaving one of the reactors, before being introduced into the subsequent one, thus limiting the increase in temperature in each reactor, for example by maintaining it at less than 40° C. In this embodiment, both the water feeding and hydrogen feeding can be partialized to the single reactors. Partialization is particularly useful as it avoids the use of an intermediate exchanger for the cooling. Two reactors are generally sufficient for keeping the temperature increase in the single reactors within the desired value.

By operating in such a way that the temperature increase in each reactor does not exceed 40° C., higher selectivities to phenol are obtained.

FIG. 1, enclosed, schematically illustrates suitable equipment for the embodiment of the process according to the plant configuration described above.

With the catalysts and most suitable operating conditions, it is possible to keep the reactor running for times which extend to various hundreds of hours, with a 100% conversion of the benzene-diols and a selectivity to phenol >95%.

By prolonging the running of the reactor, the conversion tends to be reduced, whereas the selectivity remains extremely high. In order to maintain the desired conversion degree, the reaction temperature can be progressively increased within the range of 250–500° C.

The cause of the reduction in activity is the deposit of carbonaceous material on the catalyst during the period of use in the reaction.

It has been observed that the catalysts which can be used for the purposes of the invention can be subjected without any particular problems to periodical regenerations, according to what is known in the state of the art, for the removal of the above deposits by combustion, in order to recover the initial activity.

The regeneration treatment can be effected in the same reactor in which the catalyst is charged for the reaction. The regeneration is generally carried out at a temperature ranging from 400 to 550° C. and at a pressure ranging from 1 to 3 bar, with mixtures of oxygen and nitrogen in a ratio ranging from 0.1 to 20% by volume and a space velocity (GHSV=Gas Hourly Space Velocity, expressed in 1 of gas mixture/h/l of catalyst)=3000÷6000 $h^{-1}$.

For the embodiment of a continuous process, it is preferable to have two reaction systems which are alternately inserted in reaction and regeneration.

The process according to the present invention can be conveniently used for increasing the overall yield to phenol of the process for the direct synthesis of phenol from benzene with hydrogen peroxide, a process which leads to the formation of considerable quantities of benzene-diols (U.S. Pat. No. 6,133,487 and Italian patent MI 2001A 002410).

Some illustrative examples are provided for a better understanding of the present invention and for its embodiment, which however should in no way be considered as limiting the scope of the invention itself.

PREPARATION EXAMPLES OF THE CATALYSTS

Example 1

Catalyst of the Type $Mo/Al_2O_3$.

50 g of alumina (Alumina Spheres 1.0/160 Condea-Sasol, diameter=1 mm, pore volume=0.45 ml/g minimum, surface area=150–170 $m^2/g$) are dried at 120° C. for a night. They are then impregnated with the incipient wetness technique, at room temperature, with a solution of 3.45 g of ammonium heptamolybdate dissolved in 23 g of demineralized water.

After about 2 hours of aging, the sample is dried at 140° C. for 3 hours. A further two impregnation/drying cycles are repeated and the sample is then calcined at 500° C. for 8 hours. The molybdenum content calculated, on the basis of the preparation method, is Mo=9.6% by weight.

Example 2

Catalyst of the Type $W/Al_2O_3$.

The same procedure is adopted as described in Example 1, using, instead of the solution containing molybdenum, a solution of 1.04 g of ammonium (para)tungstate dissolved in 26 g of demineralized water, the aging period is 1 hour, instead of 2 hours, and only one other impregnation/drying cycle is effected, instead of two. The calculated tungsten content is W=2.9% by weight.

Example 3

Catalyst of the Type $HPA/Al_2O_3$.

The same procedure is adopted as described in Example 1, using, instead of the solution containing molybdenum, a solution of 1.70 g of phosphotungstic acid (Acros, $H_3PO_{40}W_{12}*xH_2O$, MW=2880.17, $WO_3$ 82% min, max weight loss at 800° C.=17%) dissolved in 26 g of demineralized water, the aging period is 1 hour, instead of 2 hours. The calculated tungsten and phosphorous content, on the basis of the preparation method, is W=6.2% by weight, P=0.08% by weight.

Example 4

Catalyst of the Type $CoMo/Al_2O_3$.

The preparation is effected as for the catalyst of Example 1, but the impregnating solution was prepared using 3.45 g of ammonium heptamolybdate and 2.67 g of cobalt nitrate hexahydrate. The calculated cobalt and molybdenum content, on the basis of the preparation method, is Co=2.7% by weight, Mo=9.3% by weight.

Example 5

Catalyst of the Type $CoMoW/Al_2O_3$.

The same preparation procedure is used as for the catalyst of Example 4, but two further impregnations are effected on the final dried, non-calcined catalyst, interrupted by a drying for 3 hours at 140° C. with solutions consisting of 25 ml of demineralized water and 1.04 g of ammonium (para) tungstate. The solid is dried at 140° C. for 3 hours and then calcined at 500° C. for 8 hours. The calculated cobalt, molybdenum and tungsten content, on the basis of the preparation method, is Co=2.6% by weight, Mo=9.0% by weight, W=2.4% by weight.

Example 6

Catalyst of the Type $FeMo/Al_2O_3$.

50 g of alumina (Alumina Spheres 1.0/160 Condea-Sasol) are dried at 120° C. for a night. They are then impregnated with the incipient wetness technique, at room temperature, with a solution of 3.79 g of iron nitrate nonahydrate dissolved in 27 g of demineralized water. After about 1 hour of aging, the sample is dried at 140° C. for 3 hours. An impregnation is then effected with a solution consisting of 3.45 g of ammonium heptamolybdate and 27 g of demineralized water and the sample is dried at 140° C. for 3 hours. A further two Fe impregnation/drying—Mo impregnation/drying cycles are repeated and the sample is then calcined at 500° C. for 8 hours. The calculated iron and molybdenum content, on the basis of the preparation method, is Fe=2.5% by weight, Mo=9.3% by weight.

Example 7

Catalyst of the Type $Co/Al_2O_3$

The same procedure is adopted as described in Example 1, but the impregnating solution was prepared using 2.67 g of cobalt nitrate hexahydrate. The calculated cobalt content, on the basis of the preparation method, is Co=3.1% by weight.

Example 8

Catalyst of the Type $Pt/Al_2O_3$.

50 g of alumina (Alumina Spheres 1.0/160 Condea-Sasol) are soaked in 200 ml of demineralized water for 16 hours. After draining and 2 washings with about 100 ml of water each, the alumina is suspended, in a rotating evaporator flask, in 80 ml of an aqueous solution containing 3.2 g of a hexachloroplatinic acid solution (Pt=7.696%). The mixture is slowly rotated for 2.5 hours at 30° C. after which a solution consisting of 1.0 g of sodium formiate dissolved in 50 g of demineralized water is added. The solution is heated, again in a rotating evaporator flask with a slow rotation, to 85° C. for 90 minutes, drained, filtered and washed with about 5 l of water at 60° C. It is drained and dried for 18 h at 120° C. The calculated platinum content with respect to the catalyst, on the basis of the preparation method, is Pt=0.5% by weight.

Example 9

Preparation of Spinel Used as Carrier.

1500 ml of demineralized water, brought to pH 10 with ammonium hydroxide (32% Carlo Erba), are poured into a 5 l glass. A second solution, consisting of 203.3 g of magnesium chloride and 482.86 g of aluminum chloride hexahydrate and brought to 2 l with demineralized water, is slowly added to the ammonia solution, under stirring. During the mixing of the solutions, the pH is kept at a value of about 10 by the addition of suitable solutions of ammonium hydroxide. At the end of the addition, the mixture is kept under stirring for 2 h and the solid is aged in the mother liquor for 16 hours, filtered, washed to neutral pH of the washing water, dried at 120° C. for 16 hours. The solid is calcined at 400° C. for 16 hours and then at 600° C. for a further 16 hours. The resulting oxide is ground and sieved at between 18 and 35 mesh.

Catalyst of the Type PtZn on MgAl Spinel.

10 g of solid are impregnated with a solution consisting of 5 ml of a chloroplatinic acid solution (Pt=2 mg/ml), 1 ml of a solution of $ZnCl_2$ in water (prepared by dissolving 2.2 g of zinc chloride in 50 ml of demineralized water) and 2.5 ml of demineralized water. The impregnated solid is left to age for 16 hours at room temperature, dried at 120° C. for 16 hours and calcined at 500° C. for 16 hours. The calculated platinum and zinc content, on the basis of the preparation method, is Pt=0.1% by weight, Zn=0.2% by weight.

Commercial Catalysts

For the purposes of the present invention, catalysts available on the market for applications different from that of the invention, can be used.

It is possible to use, for example, Engelhard ESCAT™ H-60 and ESCAT™ H-50 catalysts based on cobalt-molybdenum-phosphorous and nickel-molybdenum-phosphorous, respectively, supported on alumina, which are described in technical-commercial literature provided by the manufacturer (Engelhard Italiana S.p.A.—Via Siusi 20-20132 Milan—Italy).

The catalysts Akzo Nobel KF-756 and KF-841, based on cobalt-molybdenum and nickel-molybdenum respectively, which are described in technical-commercial literature provided by the manufacturer (Akzo Nobel Chemicals S.p.A.—

Via E. Vismara 80-20020 Arese MI—Italy), can also be used, for example.

Examples of Catalytic Performances

The catalytic activity tests described in the examples were carried out in experimental laboratory equipment, in which it is possible to study the operating conditions to be adopted for the optimal running of the process. The equipment and operating procedure are described below.

Catalytic Test: Equipment and Operating Procedure

The hydrodeoxygenation reaction of the benzene-diols is carried out in vapour phase in a tubular fixed bed microreactor with the following characteristics: material=AISI 316L stainless steel, length 180 mm, $\phi_{int}$=11.5 mm, thermocouple sheath with $\phi_{ext}$=3 mm. The reactor is positioned in an oven which allows it to be brought to the temperature selected for the reaction.

The catalyst used for the test has a size of <2 mm; when a commercial catalyst produced in an industrial size is used, it is previously reduced to the desired dimensions. The catalyst charged is 5.0 g and it is positioned in the reactor between two layers of granular quartz.

The solution of benzene-diols is preheated before being charged into the upper part of the reactor, it is then vaporized and mixed with hydrogen directly in the reactor (in the layer of granular quartz), before coming into contact with the catalyst. The liquid feeding solution is dosed with a pump of the HPLC type, the flow-rate of the hydrogen is regulated with a mass flow-rate controller.

The pressure of the plant is controlled by a regulation valve situated at the outlet of the reactor.

In the activation phase of the activity test, the catalyst is heated to the reaction temperature in a stream of hydrogen, at the pressure and flow-rate established for the test, and maintained under this condition for 1 hour. Water is subsequently fed and, after 30 minutes, the actual catalytic test is initiated, with the start of the feeding of aqueous solution of benzene-diols.

The mixture of effluent vapours from the pressure regulation valve is condensed and the samples of reaction raw product are collected to evaluate the catalytic performances.

The samples are analyzed via gaschromatography and the catalytic performances are evaluated by calculating the conversion of benzene-diols and selectivity to phenol.

The regeneration of the catalyst after the activity test was effected in the same reactor used for the reaction. The operating conditions are as follows: temperature=450–550° C., pressure=1–3 bar, oxygen concentration=0.1–20% and GHSV space velocity=3000÷6000 h$^{-1}$. In particular, the treatment begins with a stream of nitrogen alone to which an equal stream of air is progressively added (in about 1 hour). The stream of nitrogen is then progressively reduced until it is finally annulled (in about 1 hour) and the treatment is prolonged for 5 to 10 hours. At the end of the treatment, the reactor is washed with a stream of nitrogen and the catalytic activity test can be re-started.

The following tables indicate examples of catalytic activity for catalysts based on elements of group VIB of the periodic table (Examples 10–23) and elements of group VIII of the periodic table (Examples 24–27). Abbreviations and notes are used in the tables, whose meaning is provided hereunder.

Abbreviations and References Used in the Examples:

1,2-BD=1,2-benzene-diol
1,4-BD=1,4-benzene-diol
BD=benzene-diols
α=WHSV, referring to the benzene-diols fed
β=time on stream, operating hours from the beginning of the catalytic test
Y=time on stream, operating hours from the last regeneration effected in the reactor
δ=conversion, referring to the sum of 1,2-BD+1,4-BD
ε=selectivity, referring to the total BD converted.

Example 10

| Operative conditions | | |
|---|---|---|
| Reaction temperature (° C.) | | 400 |
| Pressure (bar) | | 3 |
| Solvent of BD fed | | water |
| 1,2-BD in BD solution (w/w %) | | 20.0 |
| 1,4-BD in BD solution (w/w %) | | 10.0 |
| H$_2$/BD ratio (molar ratio) | | 20.5 |
| WHSV (h$^{-1}$) (α) | | 0.5 |
| Catalytic performances | | |
| Catalyst type | | Mo/Al$_2$O$_3$ |
| Catalyst preparation (see Example) | | 1 |
| T.O.S. (h) (Y) | 1 | 10 |
| Benzenediol conversion (%) (δ) | 92.5 | 32.7 |
| Selectivity to phenol (%) (ε) | 98.4 | 97.6 |

Example 11

| Operative conditions | | |
|---|---|---|
| Reaction temperature (° C.) | | 400 |
| Pressure (bar) | | 25 |
| Solvent of BD fed | | water |
| 1,2-BD in BD solution (w/w %) | | 20.0 |
| 1,4-BD in BD solution (w/w %) | | 10.0 |
| H$_2$/BD ratio (molar ratio) | | 21.2 |
| WHSV (h$^{-1}$) (α) | | 0.5 |
| Catalytic performances | | |
| Catalyst type | | Mo/Al$_2$O$_3$ |
| Catalyst preparation (see Example) | | 1 |
| T.O.S. (h) (β) | 1 | 20 |
| Benzenediol conversion (%) (δ) | 91.3 | 35.4 |
| Selectivity to phenol (%) (ε) | 92.2 | 96.9 |

Example 12

| Operative conditions | | |
|---|---|---|
| Reaction temperature (° C.) | | 400 |
| Pressure (bar) | | 25 |
| Solvent of BD fed | | water |
| 1,2-BD in BD solution (w/w %) | | 20.0 |
| 1,4-BD in BD solution (w/w %) | | 10.0 |
| H$_2$/BD ratio (molar ratio) | | 21.5 |
| WHSV (h$^{-1}$) (α) | | 0.5 |
| Catalytic performances | | |
| Catalyst type | | W/Al$_2$O$_3$ |
| Catalyst preparation (see Example) | | 2 |
| T.O.S. (h) (Y) | 1 | 25 |
| Benzenediol conversion (%) (δ) | 75.8 | 26.0 |
| Selectivity to phenol (%) (ε) | 81.8 | 90.9 |

Example 13

Operative conditions

Operative conditions as in example 12

Catalytic performances

| | |
|---|---|
| Catalyst type | $WP/Al_2O_3$ |
| Catalyst preparation (see Example) | 3 |
| T.O.S. (h) (β) | 10 |
| Benzenediol conversion (%) (δ) | 17.4 |
| Selectivity to phenol (%) (ε) | 92.4 |

Example 14

Operative conditions

| | |
|---|---|
| Reaction temperature (°C.) | 400 |
| Pressure (bar) | 3 |
| Solvent of BD fed | water |
| 1,2-BD in BD solution (w/w %) | 30.6 |
| 1,4-BD in BD solution (w/w %) | — |
| $H_2$/BD ratio (molar ratio) | 20.3 |
| WHSV ($h^{-1}$) (α) | 0.5 |

Catalytic performances

| | | |
|---|---|---|
| Catalyst type | $CoMoP/Al_2O_3$ | |
| Commercial catalyst | Escat H-60 | |
| T.O.S. (h) (β) | 1 | 20 |
| Benzenediol conversion (%) (δ) | 100.0 | 73.6 |
| Selectivity to phenol (%) (ε) | 97.2 | 99.2 |

Example 15

Operative conditions

| | |
|---|---|
| Reaction temperature (°C.) | 400 |
| Pressure (bar) | 18 |
| Solvent of BD fed | water |
| 1,2-BD in BD solution (w/w %) | 26.9 |
| 1,4-BD in BD solution (w/w %) | — |
| $H_2$/BD ratio (molar ratio) | 23.1 |
| WHSV ($h^{-1}$) (α) | 0.5 |

Catalytic performances

| | | |
|---|---|---|
| Catalyst type | $CoMoP/Al_2O_3$ | |
| Commercial catalyst | Escat H-60 | |
| T.O.S. (h) (γ) | 1 | 85 |
| Benzenediol conversion (%) (δ) | 98.6 | 100.0 |
| Selectivity to phenol (%) (ε) | 97.9 | 99.0 |

Example 16

Operative conditions

| | |
|---|---|
| Reaction temperature (°C.) | 400 |
| Pressure (bar) | 3 |
| Solvent of BD fed | water |
| 1,2-BD in BD solution (w/w %) | 15.0 |
| 1,4-BD in BD solution (w/w %) | 8.0 |
| $H_2$/BD ratio (molar ratio) | 26.6 |
| WHSV ($h^{-1}$) (α) | 0.4 |

Catalytic performances

| | |
|---|---|
| Catalyst type | $CoMo/Al_2O_3$ |

-continued

| | | |
|---|---|---|
| Catalyst preparation (see Example) | 4 | |
| T.O.S. (h) (β) | 1 | 24 |
| Benzenediol conversion (%) (δ) | 100.0 | 94.4 |
| Selectivity to phenol (%) (ε) | 96.8 | 98.3 |

Example 17

Operative conditions

Operative conditions as in example 12

Catalytic performances

| | | | |
|---|---|---|---|
| Catalyst type | CoMo | | |
| Commercial catalyst | KF-756 | | |
| T.O.S. (h) (γ) | 33 | 133 | 151 |
| Benzenediol conversion (%) (δ) | 100.0 | 98.4 | 82.5 |
| Selectivity to phenol (%) (ε) | 94.8 | 97.1 | 97.9 |

Example 18

Operative conditions

Operative conditions as in example 12

Catalytic performances

| | | | |
|---|---|---|---|
| Catalyst type | $CoMoP/Al_2O_3$ | | |
| Commercial catalyst | Escat H-60 | | |
| T.O.S. (h) (γ) | 36 | 71 | 116 |
| Benzenediol conversion (%) (δ) | 100.0 | 100.0 | 100.0 |
| Selectivity to phenol (%) (ε) | 93.2 | 96.9 | 97.5 |

Example 19

Operative conditions

Operative conditions as in example 11

Catalytic performances

| | | |
|---|---|---|
| Catalyst type | $CoMoW/Al_2O_3$ | |
| Catalyst preparation (see Example) | 5 | |
| T.O.S. (h) (β) | 1 | 15 |
| Benzenediol conversion (%) (δ) | 99.9 | 99.7 |
| Selectivity to phenol (%) (ε) | 96.8 | 95.2 |

Example 20

Operative conditions

Operative conditions as in example 11

Catalytic performances

| | | |
|---|---|---|
| Catalyst type | $FeMo/Al_2O_3$ | |
| Catalyst preparation (see Example) | 6 | |
| T.O.S. (h) (β) | 1 | 20 |
| Benzenediol conversion (%) (δ) | 99.2 | 28.3 |
| Selectivity to phenol (%) (ε) | 95.3 | 97.8 |

Example 21

Operative conditions

Operative conditions as in example 12
Catalytic performances

| Catalyst type | FeMo/Al$_2$O$_3$ | | |
|---|---|---|---|
| Catalyst preparation (see Example) | 6 | | |
| T.O.S. (h) (γ) | 2 | 45 | 97 |
| Benzenediol conversion (%) (δ) | 99.9 | 99.5 | 60.9 |
| Selectivity to phenol (%) (ε) | 97.8 | 96.9 | 97.9 |

Example 22

Operative conditions

Operative conditions as in example 11
Catalytic performances

| Catalyst type | NiMo | | |
|---|---|---|---|
| Commercial catalyst | KF-841 | | |
| T.O.S. (h) (γ) | 1 | 93 | 187 |
| Benzenediol conversion (%) (δ) | 99.8 | 100.0 | 100.0 |
| Selectivity to phenol (%) (ε) | 84.1 | 95.3 | 95.9 |

Example 23

Operative conditions

Operative conditions as in example 11
Catalytic performances

| Catalyst type | NiMoP/Al$_2$O$_3$ | | |
|---|---|---|---|
| Commercial catalyst | Escat H-50 | | |
| T.O.S. (h) (β) | 1 | 80 | 157 |
| Benzenediol conversion (%) (δ) | 99.8 | 100.0 | 99.7 |
| Selectivity to phenol (%) (ε) | 93.3 | 94.7 | 94.5 |

Example 24

Operative conditions

Operative conditions as in example 11
Catalytic performances

| Catalyst type | Co/Al$_2$O$_3$ | |
|---|---|---|
| Catalyst preparation (see Example) | 7 | |
| T.O.S. (h) (β) | 1 | 20 |
| Benzenediol conversion (%) (δ) | 69.9 | 23.2 |
| Selectivity to phenol (%) (ε) | 95.4 | 88.0 |

Example 25

Operative conditions

| Reaction temperature (° C.) | 250 |
|---|---|
| Pressure (bar) | 25 |
| Solvent of BD fed | water |
| 1,2-BD in BD solution (w/w %) | 20.0 |
| 1,4-BD in BD solution (w/w %) | 10.0 |
| H$_2$/BD ratio (molar ratio) | 6.0 |
| WHSV (h$^{-1}$) (α) | 0.9 |

Catalytic performances

| Catalyst type | Pt/Al$_2$O$_3$ | |
|---|---|---|
| Catalyst preparation (see Example) | 8 | |
| T.O.S. (h) (γ) | 5 | 15 |
| Benzenediol conversion (%) (δ) | 93.0 | 81.0 |
| Selectivity to phenol (%) (ε) | 19.1 | 36.0 |

Example 26

Operative conditions

Operative conditions as in example 11
Catalytic performances

| Catalyst type | PtZn/Spinel MgAl | |
|---|---|---|
| Catalyst preparation (see Example) | 9 | |
| T.O.S. (h) (β) | 1 | 48 |
| Benzenediol conversion (%) (δ) | 99.2 | 84.3 |
| Selectivity to phenol (%) (ε) | 46.6 | 37.8 |

Example 27

Operative conditions

| Reaction temperature (° C.) | 450 |
|---|---|
| Pressure (bar) | 25 |
| Solvent of BD fed | water |
| 1,2-BD in BD solution (w/w %) | 19.8 |
| 1,4-BD in BD solution (w/w %) | 10.0 |
| H$_2$/BD ratio (molar ratio) | 6.1 |
| WHSV (h$^{-1}$) (α) | 0.9 |

Catalytic performances

| Catalyst type | PtZn/Spinel MgAl |
|---|---|
| Catalyst preparation (see Example) | 9 |
| T.O.S. (h) (γ) | 37 |
| Benzenediol conversion (%) (δ) | 81.4 |
| Selectivity to phenol (%) (ε) | 74.7 |

What is claimed is:

1. A process for the preparation of phenol, characterized in that the phenol is obtained by the hydrodeoxygenation of a benzene-diol with hydrogen, operating continuously, in aqueous solution, at temperatures ranging from 250 to 500° C., at pressures of 1–100 bar and in the presence of a catalyst comprising an element of group VIB or their mixtures, or group VIII of the periodic table or their mixtures.

2. The process according to claim 1, wherein the benzene-diol is selected from 1,2-benzene-diol, 1,3benzene-diol, 1,4-benzene-diol and their mixtures.

3. The process according to claim 1, wherein the reaction is carried out in vapour phase at a temperature of 300–450° C., at a pressure of 3–50 bar and a space velocity expressed as kg of benzene-diols/h/kg of catalyst of 0.1–10 h$^{-1}$.

4. The process according to claim 3, wherein the reaction is carried out at a space velocity of 0.5–5 h$^{-1}$.

5. The process according to claim 1, wherein the reaction is carried out inside an adiabatic fixed bed reactor containing the catalyst, in which a stream comprising an aqueous solution of benzene-diol is fed, at concentrations ranging from 5 to 60% by weight, together with a stream of hydrogen, in such a quantity that the ratio between the total moles of hydrogen and benzene-diols ranges from 2:1 to 50:1.

6. The process according to claim 5, wherein an aqueous solution of benzene-diols is fed into the reactor, at concentrations ranging from 10 to 40% and a stream of hydrogen in such a quantity that the ratio between the total moles of hydrogen and benzene-diols ranges from 5:1 to 30:1.

7. The process according to claim 5, wherein the feeding stream is vapourized and heated to a temperature ranging from 250 to 500° C. and the pressure is kept at a value ranging from 1 to 100 bar.

8. The process according to claim 1, wherein the catalyst comprises at least one element selected from molybdenum and tungsten.

9. The process according to claim 1, wherein the catalyst comprises an element of group VIB and further comprises, as promoters, an element selected from those belonging to group VIII, phosphorous of their mixtures.

10. The process according to claim 9, wherein the catalyst comprises a promoter of group VIII selected from nickel, cobalt, iron and ruthenium.

11. The process according to claim 1, wherein the catalyst comprises at least one element selected from cobalt, palladium, nickel, and platinum.

12. The process according to claim 1, wherein the catalyst comprises at least one element of group VIII and further comprises, as promoters, an element selected from zinc, rhenium, selenium, tin, germanium, lead and their mixtures.

13. The process according to claim 1, 9 or 12, wherein the catalyst is deposited on a carrier.

14. The process according to claim 13, wherein the carrier is selected from alumina, silica, titanium dioxide, crystalline or amorphous alumino-silicates, crystalline spinels or their mixtures.

15. The process according to claim 13, wherein the catalyst based on an element of group VIB is present on the carrier at a concentration ranging from 1 to 50% by weight and the promoters of these catalysts at concentrations ranging from 0.1 to 100% atomic with respect to the element of group VIB.

16. The process according to claim 15, wherein the catalyst based on an element of group VIB is present on the carrier at a concentration ranging from 3 to 30% by weight and the promoters of these catalysts at concentrations ranging from 1 to 50% atomic with respect to the element of group VIB.

17. The process according to claim 13, wherein the catalyst based on an element of group VIII is present on the carrier at a concentration ranging from 0.05 to 20% by weight and the promoters of these catalysts at concentrations ranging from 0.5 to 200% atomic with respect to the element of group VIII.

18. The process according to claim 17, wherein the catalyst based on an element of group VIII is present on the carrier at a concentration ranging from 0.1 to 10% by weight and the promoters of these catalysts at concentrations ranging from 1 to 120% atomic with respect to the element of group VIII.

19. The process according to claim 1, wherein the reaction is carried out in two or more adiabatic fixed bed reactors in series, by cooling the stream leaving one reactor before entering the subsequent one, in order to limit the temperature increase in each reactor to a value of less than 40° C.

20. The process according to claim 19, wherein both the feeding of water and that of hydrogen are partialized to the single reactors, operating so that the temperature increase in each reactor does not exceed 40° C.

21. The process according to claim 19, wherein the reaction is carried out in two reactors which are alternately inserted in reaction and regeneration.

22. The process according to claim 1, wherein the catalysts are subjected to regeneration by means of combustion at a temperature ranging from 400 to 550° C. and a pressure ranging from 1 to 3 bar, with mixtures of oxygen and nitrogen in a ratio ranging from 0.1 to 20% by volume and a space velocity, expressed in 1 of gas mixture/h/l of catalyst, equal to 3000÷6000 $h^{-1}$.

23. The process according to claim 22, wherein the regeneration is carried out in the same reactor in which the catalyst is placed for the reaction.

\* \* \* \* \*